United States Patent [19]

Onopchenko et al.

[11] 4,406,801

[45] Sep. 27, 1983

[54] GREASE COMPOSITIONS CONTAINING QUATERNARY PHOSPHONIUM THIOSTANNATES

[75] Inventors: Judith B. Onopchenko; Gary M. Singerman, both of Monroeville, Pa.; Raynor T. Sebulsky, Kingwood, Tex.

[73] Assignee: Gulf Research & Development Company, Pittsburgh, Pa.

[21] Appl. No.: 397,606

[22] Filed: Jul. 12, 1982

[51] Int. Cl.$^3$ .............................................. C10M 1/44
[52] U.S. Cl. .............................. 252/46.7; 252/51.5 A
[58] Field of Search ......................... 252/46.7, 51.5 A

[56] References Cited

U.S. PATENT DOCUMENTS

| | | | |
|---|---|---|---|
| 2,938,869 | 5/1960 | Hugel | 252/46.4 |
| 4,104,177 | 8/1978 | Caruso | 252/51.5 A |
| 4,370,245 | 1/1983 | Ryu et al. | 252/51.5 A |

*Primary Examiner*—Jacqueline V. Howard
*Attorney, Agent, or Firm*—Deane E. Keith; Forrest D. Stine; Donald L. Rose

[57] ABSTRACT

A grease composition having improved antifriction properties and improved extreme pressure properties comprising a thickened hydrocarbon lubricating oil, calcium carbonate and a novel quaternary phosphonium thiostannate, for example, hexadecyltri-n-butylphosphonium tetrathiostannate.

8 Claims, No Drawings

GREASE COMPOSITIONS CONTAINING QUATERNARY PHOSPHONIUM THIOSTANNATES

SUMMARY OF THE INVENTION

This invention relates to grease compositions having improved antifriction and improved extreme pressure properties comprising a thickened base oil, calcium carbonate and a quaternary phosphonium tetrathiostannate or hexathiodistannate. As used herein, the expression "thiostannate" is intended as a generic expression including both the tetrathiostannates and the hexathiodistannates described herein.

DESCRIPTION OF THE INVENTION

In accordance with our invention, we have discovered that a novel class of quaternary phosphonium thiostannates is useful in substantially enhancing the antifriction and the extreme pressure (e.p.) properties of a grease composition containing calcium carbonate. The quaternary ammonium thiostannates which are useful in our novel grease formulation are defined by the formula:

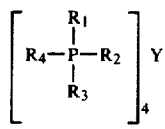

where Y is $SnS_4$ or $Sn_2S_6$; $R_1$, $R_2$, $R_3$ and $R_4$ are independently selected from alkyl, alkenyl, hydroxyalkyl and hydroxyalkenyl having from 1 to about 20 carbon atoms, preferably from about 3 to about 16 carbon atoms; and the total number of carbon atoms in $R_1$, $R_2$, $R_3$ and $R_4$ is between 4 and about 80 carbon atoms, preferably between about 16 and about 40 carbon atoms.

Examples of compounds which are defined by the above formula include:
tetramethylphosphonium tetrathiostannate,
tetramethylphosphonium hexathiodistannate,
diethyldimethylphosphonium tetrathiostannate,
tetrabutylphosphonium tetrathiostannate,
trioctylmethylphosphonium tetrathiostannate,
dilauryldimethylphosphonium tetrathiostannate,
tetradodoceylphosphonium hexathiodistannate,
dioctadecyldimethylphosphonium tetrathiostannate,
hexadecyltri-n-butylphosphonium tetrathiostannate,
dioctadecenyldimethylphosphonium tetrathiostannate,
tetrakishydroxymethylphosphonium tetrathiostannate,
and the like.

The quaternary phosphonium tetrathiostannates and hexathiodistannates used in the present invention can be prepared in accordance with the following reaction (in which any water of crystallization is ignored):

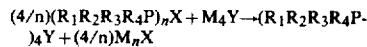

where $R_1$, $R_2$, $R_3$, $R_4$ and Y are as defined above; X is a salt-forming anion selected from chlorine, bromine, iodine, sulfate, hydrogen sulfate, lower alkyl sulfate, lower alkyl carboxylate having from 2 to about 4 carbon atoms, and the like; n is the valence of X; and M is alkali metal such as sodium, potassium, and the like, or ammonium or a mixture thereof.

The reaction is carried out in a single-phase aqueous solution when the quaternary phosphonium salt, such as tetramethylphosphonium chloride, is water-soluble. When the quaternary phosphonium salt is water-insoluble, such as hexadecyltri-n-butylphosphonium bromide, it is dissolved in a suitable water-immiscible organic solvent and reacted with the aqueous solution of the thiostannate salt in a two-phase reaction.

The two-phase process is most suitable and desirable when the quaternary phosphonium salt is substantially soluble in the organic solvent and substantially insoluble in water. However, the process is also useful if the quaternary phosphonium salt is somewhat soluble in water, provided that it is substantially more soluble in the organic solvent, such as at least about five times, preferably at least about ten times, its solubility in water at the reaction temperature. The solubility of these quaternary phosphonium salts in water depends both on the specific hydrocarbon substituents and on the specific anion. The solubility of these salts in an organic solvent also depends on these two factors as well as on the specific solvent involved. In general, the solubility of the quaternary phosphonium salt in water decreases and its solubility in the organic solvent increases as the total number of carbon atoms in this phosphonium salt increases.

The initial concentration of the quaternary phosphonium salt in the solution prior to the reaction can broadly range from about one to about 30 weight percent or higher, but preferably it will range from about five to about 20 weight percent. The initial concentration of the thiostannate salt in the solution can be between about one and about 30 weight percent, but the reaction is preferably conducted at a concentration of the thiostannate salt of between about three and about 20 weight percent.

It is preferred to carry out the reaction using quantities ranging from a stoichiometric quantity, that is a ratio of four mols of the quaternary phosphonium salt when a univalent anion is involved for each mol of the thiostannate salt, to a stoichiometric excess, such as five to ten percent or higher, of the thiostannate salt. When the reaction is carried out in this latter range, two desirable objectives are accomplished. First, efficient utilization of reactants is accomplished. And second, the quaternary phosphonium salt is fully reacted, thereby eliminating it as a potential impurity in the quaternary phosphonium thiostannate product.

The reaction mixture, after it has been suitably formed, is stirred and given sufficient time to react. Since temperature does not appear to be a particularly critical factor in the reaction, the reaction can be carried out within a range of about 20° C. to about 200° C., although we prefer a temperature range between about 50° C. and about 125° C.

The two-phase reaction is carried out by contacting the organic solution of the quaternary ammonium salt with the aqueous solution of the phosphonium salt. Although we have not studied the precise mechanism for this two-phase reaction, we believe that the desired reaction takes place at the interface between the organic phase and the aqueous phase. We find that stirring the reactant mixture, preferably with sufficient agitation to cause a substantial increase in the area of contact between the two phases, facilitates the reaction.

In this two-phase reaction, the desired quaternary phosphonium thiostannate reaction product is in the organic solution, and the by-product salt, such as sodium chloride or potassium acetate, is in the aqueous solution. This thiostannate reaction product, which can vary in nature from a dry crystalline material to a sticky amorphous mass, is recovered from the reaction mixture by first separating the two liquid phases, such as by decantation, and then evaporating or distilling off the organic solvent. When the single-phase, aqueous system is used, the desired phosphonium thiostannate precipitates out of the aqueous solution and can be readily separated from the solution and purified by water washing.

Suitable water-immiscible organic solvents for the quaternary phosphonium salt in the two-phase reaction system include aliphatic hydrocarbons having from about five to about ten carbon atoms, such as pentane, hexane, and the like; aromatic hydrocarbons and halogenated aromatic hydrocarbons having from six to about eight carbon atoms, such as benzene, toluene, chlorobenzene, and the like; halogenated aliphatic hydrocarbons having from one to about two carbon atoms, such as methylene chloride, ethylene dichloride, and the like. Also useful are aliphatic esters, such as ethyl acetate, butyl acetate, and the like; aliphatic ketones, such as isobutylmethyl ketone, diisobutyl ketone, and the like; and alkyl esters, such as diethyl ether, diisopropyl ether, and the like.

The naturally occurring fatty acids are an excellent and convenient source of the higher molecular weight alkyl and alkenyl groups in the quaternary ammonium salt used herein. As used herein, the term "alkenyl" includes mono-, di- and tri-olefinic groups. These fatty acids can be converted to the corresponding alkenyl group and saturated, if desired, by conventional hydrogenation procedures. For example, oleic acid can be converted to octadecenyl, and this can be hydrogenated to octadecyl. Since the naturally occurring fats comprise mixtures of two and generally more carbon chains of different lengths, the resulting quaternary compounds will generally contain the alkenyl and alkyl groups and the different chain lengths in the same relative proportion as the precursor acids occur in the fat.

The grease composition comprises a thickened hydrocarbon lubricating oil. Preferably the lubricating oil is thickened to a grease with a suitable substituted urea compound or mixture of substituted-urea compounds. Useful ureido compounds, their definitions, their methods of preparation and the methods of thickening oils with these compounds are disclosed in the prior art including the following patents, the disclosures of which are incorporated herein by reference. Thickeners involving aryl-substituted mono- and diureas are described in U.S. Pat. Nos. 2,710,839; 2,710,840; and 2,710,841. Various polyurea thickeners containing from two to about eight ureido groups and various alkyl or aryl radicals are described in U.S. Pat. Nos. 2,832,739 and 3,243,372. U.S. Pat. No. 4,065,395 describes a grease composition having improved high temperature properties as the result of an aryldiurea thickener composition prepared by the reaction of p-toluidine and p-chloroaniline with a toluene diisocyanate in specified proportions.

These thickeners can be represented by the general formula:

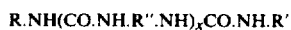

R.NH(CO.NH.R''.NH)$_x$CO.NH.R' wherein x is an integer from 0 to about 7, preferably from 1 to about 3; R and R' can be the same or different hydrocarbyl selected from aliphatic, aromatic, alicyclic and combinations thereof having from 1 to about 30 carbon atoms, preferably having from about 6 to about 20 carbon atoms and R'' is hydrocarbylene selected from aliphatic, aromatic, alicyclic and combinations thereof having from 2 to about 30 carbon atoms, preferably having from about 2 to about 18 carbon atoms. When x is greater than 1, the various hydrocarbylene groups can be the same or different.

The expressions "aliphatic", "aromatic", "alicyclic" and "combinations thereof" used in defining R, R' R'', are intended to include the presence of substituents including alkyl, aryl, halogen, alkoxy, carboalkoxy, hydroxy, carboxy, nitro, cyano, sulfonyl, amido, sulfonamide, and the like, and the term "aromatic" further is intended to include polynuclear aromatic, condensed polynuclear aromatic, and the like, all as described in the above-identified prior art.

These ureido thickeners are conveniently prepared, as described in the above-mentioned patents by the reaction of an appropriate combination of one or more monoamines and/or diamines with one or more monoisocyanates and/or diisocyanates to produce the desired composition. These amine and isocyanate reactants are brought together at an appropriate temperature in a suitable solvent with the lubricating oil itself being the preferred reaction solvent.

The amount of the substituted-urea thickener that is used is an amount sufficient to thicken the lubricating oil to the consistency of grease. Generally, at least about five percent of the thickener is used, and preferably at least about ten percent. The maximum amount of the thickener that is used is about 50 percent and preferably a maximum of about 30 percent is used.

The quaternary phosphonium tetrathiostannate or hexathiodistannate and calcium carbonate, preferably precipitated calcium carbonate, are added to the grease composition in sufficient quantity to obtain an enhancement in the antifriction and e.p. properties of the grease. The quaternary phosphonium thiostannate is used in the grease composition in a range of between about 0.3 weight percent and about ten percent, preferably a range between about 0.5 percent and about two percent. The precipitated calcium carbonate is used within a range of between about one weight percent and about ten percent, preferably a range between about two percent and about six percent.

The grease composition can contain other grease additives, as desired, in appropriate quantities to modify or improve other properties or characteristics of the grease. Thus, the grease can contain one or more additives selected from the following list: antioxidants, dispersants, anticorrosion agents, rust inhibitors, metal deactivators, antiwear agents, other extreme pressure agents, tackiness agents, dyes, and the like.

DESCRIPTION OF PREFERRED EMBODIMENTS

Example 1

A 50 g (208 mmol) sample of sodium sulfide (Na$_2$S.9-H$_2$O) and 15.8 g (59 mmol) of sodium stannate (Na$_2$.SnO$_3$.3H$_2$O) were dissolved in 140 ml of boiling water. The solution was stirred continuously for about 5 hours at a temperature of about 100° C. Following the heating, the liquid volume was reduced to about 70 ml using a rotovaporizer and was then filtered. The white crystals, which were redissolved in a minimum amount of boiling distilled water, were permitted to recrystallize at 0° C. The white recrystallized product was found, after drying, to weigh 11.0 g, a 57 percent yield of sodium thiostannate based on the sodium stannate. The mother liquor was saved and reused to increase subsequent yields.

Example 2

A 40 g (78.8 mmol) portion of hexadecyltri-n-butylphosphonium bromide was dissolved in 800 ml of toluene, and 11.04 g (29.4 mmol) of sodium thiostannate, prepared as described in Example 1, was dissolved in 800 ml of distilled water. The two solutions were placed in a two-liter flask equipped with a condenser. The mixture was heated at about 84.9° C. for about eight hours with constant stirring. The aqueous solution containing by-product sodium bromide, was then removed and the toluene layer was rinsed three times, each time with 250 ml of distilled water. Vigorous agitation was avoided during rinsing to avoid the formation of an emulsion with the product. The toluene was stripped from the solid product with a rotovaporizer. The sticky product, hexadecyltri-n-butylphosphonium tetrathiostannate, after drying to a constant weight, weighed 30 g, a 76.5 percent yield based on the quaternary phosphonium salt.

Examples 3-5

A base grease, thickened with an aryldiurea thickening composition, was tested for its extreme pressure properties by the Timken Test, ASTM D2509, before and after the addition of the quaternary phosphonium tetrathiostannate (QPTS) described in Example 2. The grease was thickened by reacting p-toluidine, p-chloroaniline and toluene diisocyanate in the lubricating oil in a mol ratio of 7:1:4. The base grease composition before addition of the thiostannate contained 75 weight percent of a heavy neutral oil, 20 percent of the aryldiurea thickener, 0.5 percent of an oxidation inhibitor, 0.5 percent of a rust inhibitor and four percent of precipitated calcium carbonate to improve the e.p. properties and extend the functional life of the grease. After the base grease was heated to 200° F. for one hour, the quaternary phosphonium tetrathiostannate was added and mixed in with a power-driven beater. The results of the Timken Tests (OK value) on the various compositions are set out in Table I.

TABLE I

| Example | Base Grease | Ex. 3 | Ex. 4 | Ex. 5 |
|---|---|---|---|---|
| Grease, wt % | 100 | 99 | 98 | 98 |
| QPTS, wt % | 0 | 1 | 2 | 2 |
| ASTM D2509, lbs. | 30 | 45 | 50 | 55 |

Examples 6-9

The quaternary phosphonium tetrathiostannate described in Example 2 was added to the same thickened grease composition used in the preceding examples, but in these experiments the effect on the Timken test of several of the other additives was also evaluated. The results of the Timken tests (OK value) on the various compositions are set out in Table II.

TABLE II

| Example | Ex. 6 | Ex. 7 | Ex. 8 | Base Grease | Ex. 9 |
|---|---|---|---|---|---|
| Thickened grease, wt % | 100 | 99 | 96 | 94.5 | 95 |
| Inhibitors, wt % | 0 | 0 | 0 | 1.50 | 0 |
| Ppt. CaCO3, wt % | 0 | 0 | 4.00 | 4.00 | 4.00 |
| QPTS, wt % | 0 | 1.00 | 0 | 0 | 1.00 |
| ASTM D2509, lbs | 10 | 10 | 40 | 30 | 60 |

The experimental results set out in Tables I and II disclose several significant features of the grease composition. First, it is shown that effective results are obtained, as shown by comparing Examples 7 and 9, by the use of the quaternary phosphonium tetrathiostannate in combination with the precipitated calcium carbonate. Second, it is shown that the oxidation and rust inhibitor package is detrimental both when the precipitated calcium carbonate but no quaternary phosphonium thiostannate is used—Example 8 compared with the base grease, and when the precipitated calcium carbonate and the quaternary phosphonium thiostannate are both used—Example 9 compared with Example 3.

It is to be understood that the above disclosure is by way of specific example and that numerous modifications and variations are available to those of ordinary skill in the art without departing from the true spirit and scope of the invention.

What is claimed is:

1. A grease composition comprising a hydrocarbon lubricating oil thickened to a grease with a substituted-urea thickener and a quantity sufficient to improve the extreme pressure properties of the grease of (a) calcium carbonate and (b) a quaternary phosphonium thiostannate having the formula:

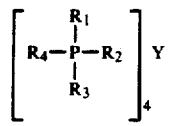

where Y is thiostannate, SnS4, or hexathiodistannate, Sn2S6; $R_1$, $R_2$, $R_3$ and $R_4$ are independently selected from alkyl, alkenyl, hydroxyalkyl and hydroxyalkenyl having from 1 to about 20 carbon atoms, and the sum of the carbon atoms in $R_1$, $R_2$, $R_3$ and $R_4$ is between about 4 and about 80.

2. The grease composition in accordance with claim 1 wherein Y is tetrathiostannate, SnS4.

3. The grease composition in accordance with claim 2 wherein $R_1$, $R_2$, $R_3$ and $R_4$ are independently selected from alkyl and alkenyl having from about 3 to about 16 carbon atoms, and the sum of the carbon atoms in $R_1$, $R_2$, $R_3$ and $R_4$ is between about 16 and about 40.

4. The grease composition in accordance with claim 2 comprising between about 0.3 and about ten weight percent of the quaternary phosphonium thiostannate and between about one and about ten weight percent calcium carbonate.

5. A grease composition in accordance with claim 1 wherein said substituted-urea thickener has the formula:

wherein x is an integer from 0 to about 7, R and R' can be the same or different hydrocarbyl groups selected from aliphatic, aromatic, alicyclic and combinations thereof having from 1 to about 30 carbon atoms, R" is hydrocarbylene selected from aliphatic, aromatic, alicyclic and combinations thereof having from 2 to about 30 carbon atoms.

6. A grease composition in accordance with claim 5 comprising between about 0.5 and about two weight percent of the quaternary phosphonium thiostannate and between about two and about six weight percent calcium carbonate.

7. A grease composition in accordance with claim 5 wherein x is 1 and R, R' and R" are aromatic having from 6 to about 8 carbon atoms.

8. A grease composition in accordance with claim 1 wherein R and R' are a mixture of p-tolyl and p-chlorophenyl in a ratio of about 3:1 to about 17:1 and R" is toluylene, $CH_3C_6H_3=$.

* * * * *